United States Patent [19]  [11] 4,400,539
Gibson et al.  [45] Aug. 23, 1983

[54] PROCESS FOR THE MANUFACTURE OF ETHYLENEDIAMINE

[75] Inventors: Charles A. Gibson; John R. Winters, both of South Charleston, W. Va.

[73] Assignee: Union Carbide Corporation, Danbury, Conn.

[21] Appl. No.: 307,215

[22] Filed: Sep. 30, 1981

[51] Int. Cl.$^3$ .................. C07C 85/06; C07C 89/02
[52] U.S. Cl. .................. 564/480; 564/477; 564/479; 564/497; 564/498
[58] Field of Search ............. 564/477, 480, 475, 479

[56] References Cited

U.S. PATENT DOCUMENTS 4,123,462  10/1978  Best ........................... 564/480

Primary Examiner—John Doll
Attorney, Agent, or Firm—Jean B. Mauro

[57] ABSTRACT

There is described a continuous process for the manufacture of ethylenediamine from the products of the reaction of ethylene oxide and ammonia, provision of a continuous recycle stream of monoethanolamine to the products of the reaction of ethylene oxide and ammonia, the amination of such products of the reaction of ethylene oxide and ammonia combined with the monoethanolamine recycle in which the feed stream to the amination reaction zone contains at least 70 weight percent monoethanolamine as well as diethanolamine and triethanolamine, the moles of ammonia provided to the amination reaction exceeds the molar concentration of alcoholic hydroxyl groups present in the amination feed, and the feed to the amination reactor contains at least a 5% increase in the concentration of monoethanolamine over the concentration of monoethanolamine in the reaction product stream from the reaction of ethylene oxide and ammonia.

8 Claims, 1 Drawing Figure

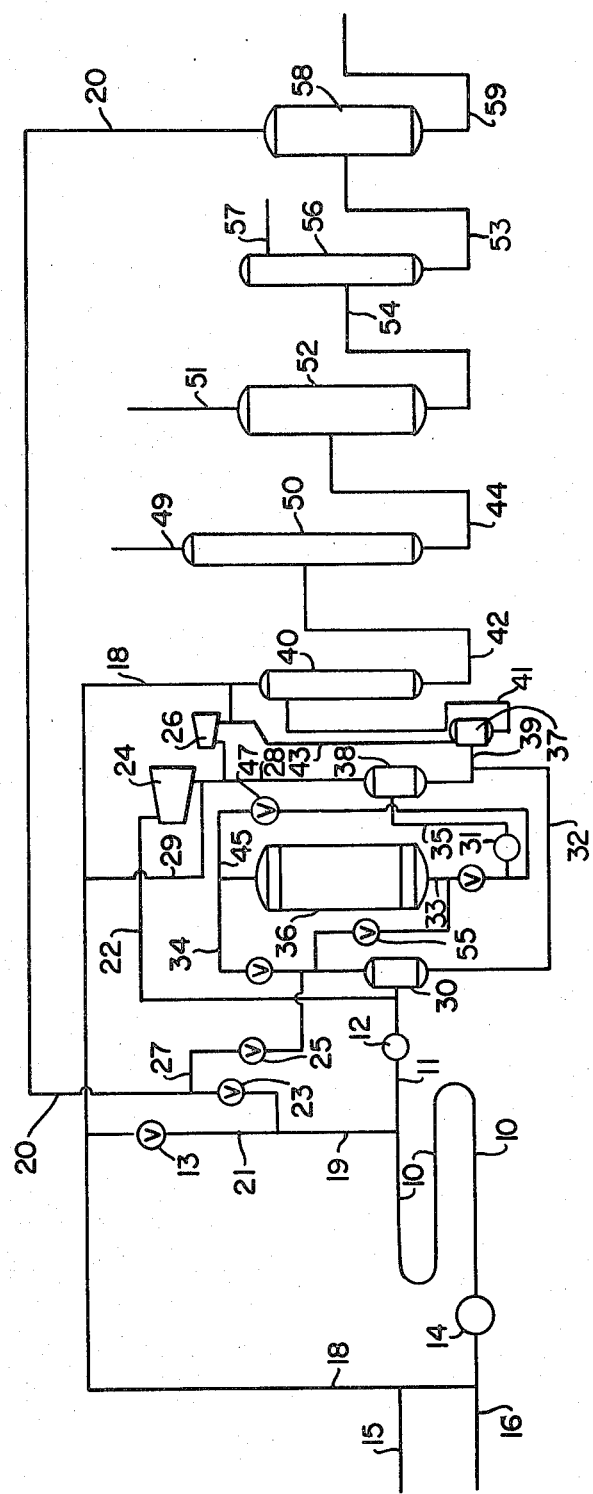

PROCESS FOR THE MANUFACTURE OF ETHYLENEDIAMINE

BRIEF SUMMARY OF THE INVENTION

1. Technical Field

This invention relates to a continuous process for the manufacture of alkyleneamines starting from the reaction of ethylene oxide with ammonia to produce a mixture of alkanolamines and the conversion of the alkanolamines by amination to ethylenediamine and other alkyleneamine products.

2. Background Art

In a private report by the Process Economics Program, Report No. 138, entitled "Alkyl Amines", by Michael Arne, of SRI International, dated March 1981, there is a section which covers the production of "Ethyleneamines from Monoethanolamine" (see pps. 81–107, 116 and 117). The author considered a substantial collection of the prior art relating to the conversion of monoethanolamine to, in particular, ethylenediamine. For example, the author considers Lichtenberger et al., U.S. Pat. No. 3,068,290, patented Dec. 11, 1962, who describe the reaction of ammonia and monoethanolamine over a nickel/magnesium oxide catalyst to give ethylenediamine; Winderl et al., U.S. Pat. No. 3,270,059, patented Aug. 30, 1966, who describe the reaction of monoethanolamine and ammonia in the presence of hydrogen over a cobalt/nickel catalyst at 150°–300° C. and 200 atm.; Johansson et al., U.S. Pat. No. 3,766,184, patented Oct. 16, 1973, who describe the reaction of ammonia and monoethanolamine to give ethylenediamine; Adam et al., U.S. Pat. No. 3,520,933, patented July 21, 1970, who describe the reaction between ammonia and monoethanolamine over a cobalt/nickel/copper/silver catalyst in the presence of hydrogen to give ethylenediamine; Corr et al., French Pat. No. 2,065,046, published July 23, 1971, who describe the production of ethylenediamine from monoethanolamine and ammonia by reaction over a cobalt catalyst containing phosphorus pentoxide and boric oxide; Boettger et al., U.S. Pat. No. 4,014,933, patented Mar. 29, 1977, who describe the reaction of ammonia and monoethanolamine over a cobalt/nickel catalyst in the presence of hydrogen; Best, U.S. Pat. No. 4,123,462, patented Oct. 31, 1978, who describes the reaction of ammonia with monoethanolamine or a mixture of alkanolamines such as one which contains 90% by weight of monoethanolamine, 7% by weight of diethanolamine and 3 weight percent of triethanolamine, in the presence of a nickel-rhenium supported catalyst; Habermann, U.S. Pat. No. 4,153,581, patented May 8, 1979, who describes the reaction of ammonia and monoethanolamine, in a mole ratio of about 7/1, in the presence of a cobalt/copper/zinc oxide catalyst at 1500 psia to produce ethylenediamine; and LeGoff et al., U.S. Pat. No. 4,209,424, patented June 24, 1980, who produce ethylenediamine from monoethanolamine and ammonia over a nickel catalyst utilizing a rhodium promoter.

The significance of the aforementioned report by Arne is its evaluation of the prior art and its interpretation, on the basis of his evaluation of the prior art, of a process for the manufacture of ethylenediamine from monoethanolamine and ammonia. According to Arne, BASF and Berol are currently producing ethyleneamines in Europe from monoethanolamine and ammonia and Union Carbide has announced a plant expansion based on the same process. Regardless of the accuracy of this statement, it is to be recognized that ethyleneamines are known to be produced from the reaction of ammonia and monoethanolamines. According to Arne, this route has the advantage of virtually eliminating the environmental problems associated with the ethylene dichloride process. In characterizing the process, Arne states that: "It has the disadvantage of producing only small quantities of polyethylene polyamines, producing instead substantial amounts of less valuable piperazine and substituted piperazines." What this means is that according to Arne, polyethylene polyamines are regarded to be valuable products and the piperazines are not regarded to be valuable products because the market for the piperazines is not large enough compared to the capacity existing for producing the same.

According to Arne, a desirable process for the manufacture of ethyleneamines would be one which would produce substantially smaller amounts of the piperazines and larger amounts of the various polyethylene polyamines.

In the analysis of the prior art that Arne relied upon, some interesting factors which induce the manufacture of the piperazines are revealed. For example, U.S. Pat. No. 3,766,184 reveals in example 10 that when diethanolamine was reacted with ammonia and water at 225° C. and 230 atm. in the presence of hydrogen gas and 7 grams of the reduced catalyst in tablet form comprising 3 to 4% each of nickel oxide, cobalt oxide and iron oxide, the remainder being aluminum oxide, 26% of the diethanolamine had been converted of which 49% had formed aminoethylethanolamine, 36% formed piperazine, and 8% formed ethylenediamine. After 5 hours of reaction, the example shows that 82% of the diethanolamine had been converted, at which 16% had been aminated to aminoethylethanolamine, 60% to piperazine, and 10% to ethylenediamine. Thus when diethanolamine is reacted with ammonia, considerably more piperazine is formed than ethylenediamine. This should be contrasted with example 17 of the same patent which reacted ammonia with monoethanolamine in the presence of water and obtained ethylenediamine as 60% of the yield of product, piperazine as 12% of the product yield, aminoethylpiperazine as 2% of the product yield and hydroxyethylpiperazine as 2% of the product yield. When diethanolamine is combined with monoethanolamine as a reactant in the process of that patent, we see from example 11 that the conversion to piperazine is intermediate of those conversions obtained in examples 10 and 17, suggesting that the presence of diethanolamine is a major factor for this increased conversion to the unwanted piperazine.

U.S. Pat. No. 4,014,933, in example 5, also demonstrates the reaction of ammonia with diethanolamine. In that example, the patentees obtained a product composition comprising 4% ethylenediamine, 22% of piperazine, 17% of aminoethylethanolamine, and 54% of unreacted diethanolamine. Essentially the same results can be seen in example 8 of German application No. 1,950,604, published Apr. 22, 1971.

The aforementioned examples which clearly demonstrate the propensity of diethanolamine to react with ammonia to produce a disproportionate amount of piperazines is further demonstrated in U.S. Pat. No. 3,766,184. By comparing examples 11 and 17 of the patent, we find that the presence of diethanolamine and triethanolamine in the reaction feed, as demonstrated in example 11, contribute to the formation of a disproportionate amount of piperazine. It should be noted in the case of example 17 that the feed was ammonia with monoethanolamine and the amount of the piperazines which were formed constituted essentially 1/10th the amount of the ethylenediamines formed. In example 11, the piperazines, which were formed constituted about 1/5th the amount of the ethylenediamine which was formed. However, in example 17 the process was operated in such a manner as to favor the formation of piperazine; note that the monoethanolamine conversion in example 17 was 55% which indicates a longer reaction time thus favoring high conversions which "leads to lower selectivity to the desired ethylenediamine and to more of the undesirable piperazine", see Arne, pg. 83, supra.

This would suggest that the presence of diethanolamine and/or triethanolamine in the feed along with monoethanolamine contributes to the formation of an amount of piperazine which exceeds that which would be obtained from monoethanolamine alone. It also suggests that the amount of the piperazines formed exceeds that amount which the amount of diethanolamine and/or triethanolamine, per se, would form under the reaction conditions employed. This being the case, it it logical to assume that diethanolamine and/or triethanolamine are in some manner reacting with monoethanolamine or inducing the unfavorable reaction of monoethanolamine so as to form increased amounts of the unwanted piperazines.

The foregoing analysis also suggests that while the manufacturing of alkyleneamines from monoethanolamine reaction with ammonia is sound, if one were to utilize a reaction feed of monoethanolamine combined with diethanolamine and/or triethanolamine, more of the unwanted piperazines would be produced and this would constitute an economic loss.

However, the use of monoethanolamine alone is not without its disadvantages. It is known that monoethanolamine is formed by the reaction of ammonia and ethylene oxide and the products of that reaction constitute a mixture of monoethanolamine, diethanolamine and triethanolamine. If monoethanolamine has to be isolated before it is utilized in the manufacture of the alkyleneamines, it means that the monoethanolamine must be distilled from the product mixture in which it is formed and this adds to the cost of the monoethanolamine. Moreover, such monoethanolamine, when recovered, is brought to room temperature and when it is subsequently utilized in the formation of the ethyleneamines, it has to be heated and pressurized to the conditions utilized for the manufacture of the alkyleneamines. Consequently, there is a considerable energy cost involved in the effective utilization of monoethanolamine per se. It should also be appreciated that the ammonia which is utilized in the reaction to produce the monoethanolamine is not directly available for the reaction to produce the alkyleneamines unless it is subjected to the same treatment of heating and pressurization as is the monoethanolamine.

DISCLOSURE OF INVENTION

There is described herein a continuous process for the manufacture of ethylenediamine, as well as other ethyleneamines, which comprises providing a continuous homogeneous fluid stream under pressure, which stream comprises ammonia, monoethanolamine, diethanolamine and triethanolamine as produced by the direct reaction of ethylene oxide and ammonia. The stream contains ammonia in an amount such that the number of moles thereof substantially exceeds the molar concentration of alcoholic hydroxyl groups present in the stream. The process also involves providing a continuous recycle stream consisting essentially of monoethanolamine, provides for an amination zone comprising a solid amination catalyst, and a separation zone for separating monoethanolamine from the amination product stream removed from the amination zone. The monoethanolamine which is separated from the amination product stream forms the aforesaid recycle stream. The recycle stream is fed under pressure to the amination zone by combining it with the aforesaid fluid stream to form a continuous amination feed stream which is under pressure. This amination feed stream is supplied to the amination zone which is maintained at a superatmospheric pressure but sufficiently below the pressure of the amination feed stream to assure flow thereof through the amination zone and to form an amination product stream containing ethyleneamines therein. The ethyleneamines are continuously recovered from the aforesaid amination product stream. The amination feed stream provided contains at least 70 weight percent of monoethanolamine based on the weight of the ethanolamines contained therein. The moles of ammonia in the amination feed stream exceeds the molar concentration of alcoholic hydroxyl groups in said amination feed stream. The amination feed stream also contains at least a 5% increase in the concentration of monoethanolamine over that which is contained in the aforesaid homogeneous fluid stream.

The process of this invention provides a number of advantageous novel features. For example, one may utilize in the amination reaction a product stream obtained directly from an ethanolamines reactor (which involves the reaction of ethylene oxide with ammonia as aforedescribed) and thereby reduce significantly the raw material and energy costs attendant in the formation of alkyleneamines. As a consequence of doing this, there is provided to the amination reaction a feed stream which contains diethanolamine and triethanolamine. This invention gives recognition to the fact that by maintaining a concentration of monoethanolamine in the feed stream to the amination zone at a level greater than is provided by the reaction of ethylene oxide and ammonia, that one can enhance the capacity in the amination zone to reduce the formation of the piperazines. This is believed to occur by virtue of diluting the product stream from the ethylene oxide and ammonia reactor, i.e., the homogeneous fluid stream, with monoethanolamine whereby to materially reduce the affect that diethanolamine and/or triethanolamine have on enhancing the formation of the piperazines.

The process of this invention achieves a production cost advantage of at least 20% over the production cost of producing ethyleneamines by the ethylene dichloride-ammonia process. Giving proper credits for piperazines, the process of this invention gives substantially greater return on investment and net income, even on an after tax basis, than the ethylene dichloride-ammonia process.

DETAILS OF THE INVENTION

Reaction Between Ethylene Oxide and Ammonia to Form Alkanolamines

The process which may be employed to provide a product stream of alkanolamines by the reaction of ethylene oxide and ammonia, viz. the aforementioned continuous homogeneous fluid stream, may be any one of the processes described in the prior art which involve the reaction of ethylene oxide with ammonia to produce a mixture of monoethanolamine, diethanolamine and triethanolamine. A desirable process from the standpoint of this invention is one which produces a mixture in which monoethanolamine is present in amounts greater than 50 weight percent of the total concentration of alkanolamines. Illustrative of such processes are those described in U.S. Pat. No. 2,196,554, U.S. Pat. No. 3,697,598, and U.S. Pat. No. 3,723,530.

The process in U.S. Pat. No. 2,196,554 to Guinot involves preparing monohydroxylethylamines in yields of 90%–95% by reacting at least 30 parts by weight of ammonia with 1 part of ethylene oxide in a liquid phase reaction. Relatively dilute aqueous ammonia solutions are employed and the patent discloses that steam generated during concentration of the reaction product mixture is used for heating subsequent reaction product mixtures to separate ammonia gas therefrom, thus reducing the heat energy requirements for the process. In the practice of the instant invention, when utilizing the reaction of this patent it will not be necessary to separate the ammonia gas from the product mixture since ammonia gas will be utilized in the amination step resulting in the formation of the ethyleneamines.

Another process for preparing ethanolamines with extremely high yields of monoethanolamines and only small amounts of the di- and triethanolamines by reacting ethylene oxide with large excess amounts of ammonia in a liquid phase reaction system is disclosed in U.S. Pat. No. 3,697,598 to Weibull, et al. The relative molar ratio of ammonia to ethylene oxide used in the process is within the range of 10:1 to 80:1 with the reaction being carried out in the presence of a cation exchange resin catalyst. The process of this patent is described as being a continuous process which is capable of being run isothermally or, preferably adiabatically, at temperatures in the range of 20° C. to 250° C. when pressures are employed that are high enough to keep the reactants and reaction products in the liquid phase throughout the reaction.

U.S. Pat. No. 3,723,530 to Goetze et al. also discloses a process for preparing a mixture of alkanolamines by the liquid phase reaction of ethylene oxide and a large excess of ammonia. In this patent the mole ratios of ammonia to ethylene oxide are from 14:1 to 40:1. The patent describes the process as being capable of being run continuously, either isothermally or adiabatically. When operated continuously, the reaction is carried out in the liquid phase at temperatures in the range from 60° C. to 150° C. and pressures of 20 to 120 atm., and the monoethanolamine content of the product mixture generally does not exceed 70% by weight.

The preferred method for making ethanolamines is set forth in copending applications Ser. Nos. 247061, filed Mar. 24, 1981, and 259,899, filed May 4, 1981. These applications disclose processes for preparing alkanolamines in which high yields of monoalkanolamines are obtained. The processes involve the reaction of, e.g., ethylene oxide with a large excess of ammonia in a single supercritical fluid phase. The process disclosed in said applications is capable of being run batchwise or continuously under isothermal or adiabatic conditions. When the process is operated as a continuous process, the desired reactor is of a design which provides for the minimization of produce recycle and thereby maximizes the production of the desired ethanolamines, minimizing the formation of higher molecular weight ethanolamine products. The preferred process for making the ethanolamines involves reacting a homogeneous stream of a mixture of ethylene oxide and ammonia in a molar ratio of ammonia to ethylene oxide within the range between about 15:1 and about 50:1. The stream is maintained in a single, homogeneous, supercritical fluid phase by maintaining a temperature and pressure which creates such a phase. The temperature for effecting the supercritical fluid is that temperature which constitutes the minimum critical temperature for the fluid composition. Typically, the supercritical fluid phase has a density of at least 15 pounds per cubic foot. This supercritical fluid phase is maintained for a period of time sufficient to permit the reaction to proceed to completion and thus to form a product mixture containing predominantly monoethanolamine (frequently at least about 70 weight percent of the composition of the ethanolamines) and small amounts of the di- and triethanolamine.

In practicing this preferred process for making the ethanolamines, the temperatures employed to carry out the reaction between ethylene oxide and ammonia is preferably above the critical temperature of the reaction mixture. When maintained at that temperature, a single supercritical fluid phase is achieved within which the reaction between ethylene oxide and ammonia will occur. The reaction proceeds when the reaction mixture is maintained above its critical temperature to achieve the single supercritical fluid phase. If one increases the pressure of the reaction zone, then there will be a consequent increase in the reaction rate. An increase in pressure is reflected by an increase in the density of the supercritical fluid phase. The degree of increase in the density of the reaction mixture is only important as it relates to the reaction rate, but in terms of practicing the preferred process for making the ethanolamines it is only necessary that the reaction mixture be maintained as a single phase supercritical fluid. In the typical case, the density of the single phase supercritical fluid will be at least 15 pounds per cubic foot (240 kg/m$^3$).

The reaction may be carried out under isothermal or, preferably adiabatic conditions, and while no catalyst is required the presence of a small amount of water in the reaction mixture has an advantageous catalytic effect. In the most preferred embodiment, it is desirable to effect the reaction in a plug-flow type reactor by feeding a stream comprising ammonia and ethylene oxide to one end of a tubular plug-flow type reactor and withdrawing the effluent containing the desired alkanolamines from the other end thereof. It is also very desirable in the practice of the invention to maximize the plug-flow characteristics of the reactor and for this reason the geometry of the reactor should be such as to minimize any backmixing or recycling that might occur as a consequence of improper reactor design or improper fluid velocities.

In making the ethanolamines, it is preferred that a large excess of ammonia relative to the ethylene oxide be used in the reaction to obtain yields of monoethanolamines of at least 65 weight percent, preferably at least 70 weight percent and worst. In a typical practice of the invention in order to obtain these desirable yields of monoethanolamine, one may employ between about 15 to about 50 moles, and preferably between about 20 to 35 moles, of ammonia for each mole of ethylene oxide.

As indicated above, the temperature at which the reaction between ethylene oxide and ammonia is carried out is important if one operates the reaction such that the reaction mixture is maintained in single supercritical fluid phase during the course of the reaction. As pointed out previously, the temperature should be above the critical temperature for the reaction mixture in order to achieve the supercritical fluid phase. The temperature should be above 130° C. and may be as high as 225° C. though the upper limit of the reaction temperature is not critical so long as the critical temperature of the reaction mixture is exceeded. In the most preferred embodiment, the reaction temperature is within the range from about the critical temperature of the reaction mixture, generally from about 130° C. to about 225° C. Under isothermal conditions, since the reaction is strongly exothermic, it is necessary to withdraw heat from the reaction mixture to keep the temperature approximately constant.

In cases where the reaction is to be carried out under adiabatic or nearly adiabatic conditions, the reactants are preheated to a temperature which is at least sufficient to effect an interreaction between the reactants, such as a temperature as low as 20° C. and higher. It should be understood that if one attempts to effect the reaction at such low temperatures as 20° C. that such will not occur with the reaction mixture being in a single supercritical fluid phase and therefore it will be necessary to preheat and/or utilize the exotherm of the reaction to achieve conditions which would bring the reaction mixture under supercritical fluid conditions as aforestated. However, in the desirable practice of this invention the reactant mixture is introduced at a temperature such that they achieve a supercritical fluid condition. Under such conditions, the reaction occurs rapidly with a strong exotherm. In the typical case, the reactant mixture is heated and introduced to the reaction zone at a temperature sufficient to achieve the supercritical fluid conditions. The pressure of the reaction zone, coupled with its temperature, should be such as to achieve the supercritical fluid state. Desirably, the pressure throughout the course of the reaction maintains the single phase supercritical fluid state. The pressures applied in the reaction of ammonia with ethylene oxide is within the range of about 2000 pounds per square inch absolute (psia) to about 5000 pounds per square inch absolute (psia).

Though the reaction of ethylene oxide and ammonia under supercritical fluid conditions need not be carried out in the presence of any particular catalyst, it has been found advantageous as characterized in the aforementioned copending applications to effect that reaction in the presence of a small amount of water incorporated with the reaction mixture. It has been found that such a small amount of water has an advantageous catalytic effect on the reaction rate for forming ethanolamines though it does not appear to affect the yield of monoethanolamine in the product mixture. The amount of water than can be used to affect catalytic activity is not a critical amount, and therefore only small amounts of water are utilized to effect this kind of result. In general from about 0.5% to about 5% by weight of water based on the weight of the reaction mixture may be utilized to catalytically induce the reaction. Though greater amounts of water may be desirable or useful to affect the aforementioned catalysis, such amounts need not be employed and indeed, in the typical case, they should be avoided to limit the energy requirements needed to separate water from the product mixture.

In this embodiment, before carrying out the reaction of ethylene oxide with ammonia, the process (as pointed out previously) is carried out continuously under isothermal or, preferably adiabatic conditions, in a plug-flow type reactor or a series of reactors which in combination achieve the results of a plug-flow type reaction system. A turbulent single directional flow of the reaction mixture through a plug-flow type reactor, under plug-flow type reaction conditions, results in the flow of the stream through the reactor with a minimum amount of backmixing and thermal stratification. This results in essentially eliminating hot spots in the reactor which will affect the reaction rates and product distribution, i.e., as between monoethanolamine, diethanolamine and triethanolamine, and minimize the reaction of ethylene oxide with already formed ethanolamines.

THE AMINATION REACTION

The amination reaction employed in carrying out the process of this invention is not narrowly limited provided that the objectives of the invention are obtained. To that extent, one may employ the technology of Arne Lichtenberger et al., Winderl et al., Johansson et al., Adam et al., Corr et al., Boettger et al., Habermann and LeGoff et al. to produce ethylenediamine from the product mixture derived from the reaction of ethylene oxide with ammonia, as hereinabove described.

However, in the preferred practice of this invention, the amination process is carried out in such a manner as to favor the selectivity of the reaction towards the production of ethylenediamine. This is accomplished by utilizing the nickel-rhenium catalyst which are described in the aforementioned Best patent and U.S. Pat. No. 4,111,840, patented Sept. 5, 1978, to Best.

Broadly speaking, the objective of the amination reaction is to convert the products of the reaction of ethylene oxide and ammonia, which products contain, inter alia, monoethanolamine, diethanolamine and triethanolamine, to ethyleneamines. In the typical practice of the invention, the amination reaction serves to convert such products to, inter alia, ethylenediamine. As mentioned above the reaction of ethylene oxide and ammonia produces a stream which contains essentially ammonia, monoethanolamine, diethanolamine and triethanolamine. The amount of ammonia in the product mixture is subject to the amount of ammonia which is utilized in the reaction with ethylene oxide. In the typical case the amount of ammonia which will be used will be vastly in excess of the stoichiometry of the reaction to produce the product mixture and therefore the available ammonia which is used in the reaction between ethylene oxide and ammonia will in large part be adequate for the subsequent amination reaction to produce the ethyleneamines. The aforementioned mixture of ammonia, monoethanolamine, diethanolamine and triethanolamine will comprise the continuous homogeneous fluid stream mentioned previously. The homogeneous fluid stream can be supplied directly to the amination reaction. In practicing the process of this invention there is provided with the homogeneous fluid stream additional monoethanolamine as described above and that additional amount of monoethanolamine with the homogeneous fluid stream when provided to the amination reaction will comprise the amination feed stream.

As mentioned previously, the amination feed stream is supplied to the amination zone at a pressure which is equal to or somewhat lower than the pressure of the homogeneous fluid stream. Consequently, the amination reaction zone is at a pressure which is essentially equivalent to the pressure of the amination feed stream as it exists when introduced to the amination reaction zone.

In the typical case the amination feed stream will be composed of the components of the homogeneous fluid stream, recycled monoethanolamine and, optionally, hydrogen and/or ammonia. In the preferred operation of the process of this invention the amination feed stream is supplied to the amination reaction as a single phase supercritical fluid stream. However, the pressure of that supercritical fluid stream will be less than the pressure of the continuous homogeneous fluid stream which is removed from the reaction between ethylene oxide and ammonia, even though the latter stream is also in the typical case a single phase supercritical fluid stream.

The amination zone comprises as an essential ingredient in order to effect the amination reaction a catalyst material which will convert the aforementioned amination feed stream into a stream containing ethyleneamines, preferably containing inter alia ethylenediamine. Such material effects the production of the ethyleneamines, as aforedescribed, preferably favoring the formation of ethylenediamine. Though the catalysts which are generally described in the prior art as capable of converting a mixture of ammonia and monoethanolamine in the vapor state to ethylenediamine may be utilized in the practice of this invention, the preferred catalyst is a solid material comprising nickel and rhenium on a support as described in the aforementioned Best patents. Such catalyst is characterized as having high activity and selectivity in amination processes and comprises rhenium and nickel impregnated on a support material such as alpha-alumina, silica, silica-aluminas, kieselguhrs or diatonaceous earths, and silica-titania, in which the mole ratio of nickel to the rhenium is in the range of 2:1 to about 30:1 and the total nickel and rhenium metal present is in the range of 3 to 30 percent by weight of the support. Such catalysts are discussed at length in U.S. Pat. No. 4,123,462 and such disclosure for their manufacture is incorporated herein by reference, and in particular that disclosure set forth in column 4, lines 24–34, that disclosure starting at column 5, line 59, all of columns 6, 7, and 8 to line 23 of column 9, Examples 2, 3, 4, 5, 6, 7, 8, 9, 10 and 12. The same disclosure can be found in U.S. Pat. No. 4,111,840, patented Sept. 5, 1978, and that disclosure is also incorporated herein by reference.

The amination feed stream contains at least 70 weight percent monoethanolamine based on the total ethanolamines content, not more than about 30 weight percent diethanolamine, same basis, not more than 15 weight percent of triethanolamine determined on the same basis, and the sum of the diethanolamine and triethanolamine does not exceed 30 weight percent of the total ethanolamine content thereof. The amination feed stream also contains ammonia in an amount which is in stoichiometric excess of the alcoholic hydroxyl groups which are present in the amination feed stream. In the preferred case there is contained at least 10 moles of ammonia for each mole of ethanolamine present in the amination feed stream. In the most preferred embodiment there is provided at least 15 moles of ammonia from each mole of ethanolamine provided in the amination feed stream and the utilization of at least 20 moles of ammonia for each mole of monoethanolamine which is present in the amination feed stream being the most highly preferred embodiment. The amination feed stream may also possess a limited amount of water. The water that is present will typically be that which is provided as a result of the ethylene oxide-ammonia reaction. The water content in the amination feed stream may range between 0 weight percent to 10 weight percent, basis the weight of the amination feed stream and preferably the water content is kept between 0–5 weight percent, based on the total weight of the amination feed stream.

In further characterizing the amination feed stream, the preferred monoethanolamine content thereof is at least 90% of the weight of the total ethanolamines contained therein, while the diethanolamine content of the amination feed stream is typically at least 3% of the weight of the aforementioned total ethanolamines content. Usually the triethanolamine content of the amination feed stream is at least 0.5% by weight of the total ethanolamines content.

The reaction which involves the amination feed stream to produce ethyleneamines is accomplished in the amination zone. This zone contains the solid catalyst in the form of a fixed bed and has a temperature and pressure sufficient to cause the amination feed stream to react to form the ethyleneamines, such as ethylenediamine, etc. The amination zone contains the appropriate catalysts for the amination reaction, as described above, the amination feed stream, hydrogen and ammonia. When hydrogen and ammonia are not components of the amination feed stream in the appropriate proportions, optionally, they are added separately.

The hydrogen may be supplied to the reaction zone as a separate feed stream into the amination zone or as a component of the amination feed stream. Hydrogen serves the purpose of a promoter for the catalyst. When hydrogen is not provided in the reaction zone and the catalyst is a nickel-rhenium catalyst as described above, the catalyst life is greatly shortened and the rate of amine production is materially reduced. By providing hydrogen in the amination zone, the catalyst is continuously promoted to effectively cause the amination of the ethanolamines to produce the desired products. It is believed that hydrogen acts in part as a continuously supplied inert to keep available sites at the catalyst surface for the desired reaction between ammonia and the ethanolamines and preclude the stabilization of the catalyst sites by ethyleneamines and/or ammonia. Inerts which can also be supplied to the reaction are inert gases such as nitrogen, helium, methane, and the like. Such inert gases can be utilized to help in the control of the reaction temperature and assist in maintaining the desired pressure conditions during the course of the reaction. Suitable inert solid diluents for the catalyst can be any of the aforementioned support materials utilized in the manufacture of the catalyst and preferably is a material such as alpha-alumina, silicon carbide, silica, glass shot or balls, and the like. Such solid inert materials serve the purpose of adequately diluting the bed for the purpose of controlling gas flow characteristics within the catalyst bed as well as assisting in the control of the temperature within the reaction zone.

As mentioned immediately above, the catalyst is provided in the reaction zone in the form of a bed of particles. Typically, such beds are supported upon distribution plates or screens which allow for the passage of gases or fluids through the bed. In this respect, the process is carried out utilizing standard fluid-solid heterogeneous catalytic techniques.

Also supplied to the amination zone is an amount of monoethanolamine in addition to that which is supplied to the amination feed stream from the homogeneous fluid stream. This monoethanolamine is provided to the amination zone in admixture with the amination feed stream, and therefore becomes a part thereof either immediately prior to the feeding of the amination feed stream to the amination zone or at some point further upstream of the amination zone.

As mentioned previously, hydrogen is supplied as a promoter for the catalyst. The amount of hydrogen that should be present in the amination feed stream should be from about one mole percent to about 30 mole percent based on the total moles in the amination feed stream. Preferably the amount of hydrogen which is provided in the amination zone is from about 2 to about 15 mole percent based on the total moles in the amination feed stream.

The temperature of the amination zone in the usual case is selected based upon the temperature characteristics of the catalyst which is utilized for the amination reaction. When employing the nickel-rhenium catalyst mentioned above, this temperature is about 120° C. to about 225° C., preferably in a range of about 150° to about 215° C. It should be mentioned that in carrying out the process in its most desirable embodiment, the stream within the amination zone is under supercritical fluid or vapor phase conditions, preferably under supercritical fluid conditions as described above. Therefore, the pressure within the reaction zone should be correlated with the temperature so as to achieve either the supercritical fluid conditions or a vapor phase condition. It is most desirable to avoid the presence of any liquid on the catalyst. That is, the catalyst should be essentially free of any liquid deposition on its surface. If such deposition occurs, it will very rapidly cause the dissolution of the catalyst on the surface of the supported used with it and consequently the catalyst will become liquefied and be carried away with the effluent from the amination zone. As that occurs, the catalyst within the zone will contain less and less of the desired nickel and rhenium, and consequently its activity will decrease to such an extent that eventually it will no longer activate the amination reaction.

In carrying out this process, in a preferred embodiment utilizing a nickel-rhenium catalyst which also contains boron, as described in the aforementioned Best patents, the pressure is in the range of about 1500–3000 psi, with the preferred pressure being approximately 2250 psia. When operating at such pressures, the temperature is in the range of about 150°–215° C. and the fluid velocity through the amination zone is carried out to effect a residence time in the reactor of from about 3 to 8 minutes.

The amination reactor which provides the amination zone may be any reactor configuration ranging from a fixed bed tubular reactor to a backmixed fixed bed reactor. In view of the fact that the amination reaction does not provide a significant exotherm, it is not necessary for one to utilize a fluid bed reactor. However, one may utilize a fluid bed reactor if such is desired. One important feature of a reactor is that it should be designed to provide for a uniform flow distribution of the amination feed stream (and hydrogen, ammonia, and the like gases, to the extent that such are not included with the amination feed stream) to the reaction zone. The better interdispersion of the various components of the amination feed stream (as well as hydrogen, ammonia and other gases supplied to the amination zone) the better will be the overall effectiveness of the amination reaction.

After the fluids are removed from the amination zone, they are subjected to a variety of separation steps for the purpose of removing the various components contained therein. For example, the effluent gas stream from the amination zone will be subjected to distillation to remove water, ammonia ethylenediamine, monoethanolamine (which will be recycled as described above), hydroxyethylpiperazine, aminoethylethanolamine, tetraethylenepentamine, diethylenetriamine, aminoethylpiperazine, piperazine, triethylenetetramine, diethanolamine and triethanolamine. Because of the vast differences between the boiling points of monoethanolamine, diethanolamine and triethanolamine, the separation of monoethanolamine from the composition is very readily obtained and an extremely pure stream of monoethanolamine can be produced by simple distillation. In the normal course, the monoethanolamine which can be obtained by distillation will contain at least 99 weight percent of monoethanolamine with extremely small amounts of piperazine, diethylenetriamine, aminoethylpiperazine, hydroxyethylpiperazine, and the like, being present.

HIGH PRESSURE SEPARATION

In a preferred embodiment of this invention, the homogeneous fluid stream which comprises the effluent from the reaction of ethylene oxide and ammonia is introduced to a high pressure separator which serves the purpose of producing an amination feed stream which is enriched in respect to its monoethanolamine content without creating a significant energy loss resulting from a large pressure reduction. In essence, what occurs is that the homogeneous fluid stream is passed to a simple separation tank in which a modest phase separation occurs resulting in the removal from the tank of a gaseous stream which is richer in monoethanolamine than the homogeneous fluid stream which is provided to the tank. Withdrawn from the bottom of the tank is a stream which contains a smaller content of monoethanolamine. In a preferred embodiment of the invention, this high pressure separation is practiced as follows. The homogeneous fluid stream which is removed from the reaction between ammonia and ethylene oxide is passed as a supercritical fluid to admixture with monoethanolamine recycle introduced at a temperature substantially below that of the homogeneous fluid stream. As a result, the temperature of the homogeneous fluid stream is reduced and the resulting stream that is formed from admixture with the recycled monoethanolamine is no longer in a supercritical fluid condition. That stream is thereafter passed to a heat exchanger and the temperature of the stream is raised to a temperature which allows the enriched amination feed stream which is taken from the high pressure separator tank to be again a supercritical fluid stream. For example, if the effluent from the ethylene oxide-ammonia reaction, which comprises the continuous homogeneous fluid stream, is at 170° C., it will be cooled by recycled monoethanolamine which is at about 45° C. to form a lower pressure stream having a temperature of about 143° C. which is no longer a supercritical fluid. That stream is thereafter heated to form an effluent from the high pressure separator tank having a temperature of 160° C. and consequently being further heated to a stream having a temperature of 180° C., and possessing the conditions of a supercritical fluid. It also follows that by introducing the recycled monoethanolamine into the fluid stream followed by high pressure separation that there is a loss of pressure from that at which the homogeneous fluid stream is at when taken as an effluent from the ethylene oxide-ammonia reaction. As described previously, that reaction is carried out at pressures within the range of about 2000 pounds per square inch absolute to about 5000 pounds per square inch absolute. For example, should the effluent from the ethylene oxide-ammonia reaction be at 3000 psi, it typically will be reduced to a pressure of about 2200 psi before it is fed to the high pressure separator tank and reheated through a heat exchanger to a temperature which achieves a supercritical fluid condition.

The high pressure separator tank is nothing more than a simple tank containing therein a demister pad at its upper area to remove any liquid components trapped in the volatile components removed from the upper portion of the tank. The liquid body which is created in the tank as a result of the phase separation occurring therein will be removed from the bottom thereof and will be richer in diethanolamine and triethanolamine than is the homogeneous fluid stream minus any amount of ethanolamine which has been added to such stream prior to its addition to the high pressure separator tank.

The monoethanolamine recycle which is provided can be an amount which is equivalent to the amount of monoethanolamine not converted in the amination zone to ethyleneamines. The monoethanolamine recycle can be introduced before or after the aforementioned high pressure separation, but at least, in any case prior to the amination zone in admixture with the amination feed stream. If it is introduced prior to the amination zone to the components of the amination feed stream, then for the purposes of this invention, it is considered a part of the amination feed stream and to the extent that the previous discussion refers to a supply of an amination feed stream to the reaction zone, such additional monoethanolamine is considered a component part thereof. In the preferred practice of this invention, the monoethanolamine is removed from the product stream effluent from the amination zone after the removal of piperazine, and this monoethanolamine recycle is reduced in temperature from about 60° C. to about 25° C. and has a purity as aforedescribed. The monoethanolamine is recycled back to a point in the reaction chain prior to the high pressure separator to effect admixture with the homogeneous fluid stream as described previously. It is also possible to instead recycle at least a part of the monoethanolamine stream subsequent to the high pressure separation step so that it is not necessary to reduce the temperature of the monoethanolamine prior to its reintroduction as a recycle stream into the ethanolamine feed going to the amination zone. In such a case, where there is effected monoethanolamine enrichment by the utilization of a high pressure separation step, as described above, then the homogeneous fluid stream is cooled by heat exchanger to a temperature low enough to take it from a supercritical fluid stream to a liquid stream which allows separation to occur in the high pressure separation tank.

Coming now to the drawing, the drawing illustrates a schematic flow diagram of an integrated process for carrying out this invention which includes the separation of products from the amination reaction to the extent necessary to allow for the recovery of monoethanolamine for recycle.

Excluded from the drawing is the recovery of other components of the amination reaction as well as diethanolamine and triethanolamine. Their individual separation is effected by conventional distillation techniques and the order of their separation is predicated upon the respective volatilities of such components.

As shown in the drawing, ethylene oxide for the reaction is fed through line 16 into admixture with ammonia recycle fed through line 18. Makeup of ammonia is supplied through line 15 into line 18 on an as needed basis. The admixture of ammonia and ethylene oxide is achieved simply by connecting the respective lines for each and they are pumped (not shown) with a high pressure feed pump to heat exchanger 14.

In order to effectively utilize the energy resources of the process, the reaction mixture stream comprising ethylene oxide and ammonia are fed through a high pressure feed pump (not shown) to a shell and tube heat exchanger 14, which is supplied with heat by passing the effluent from the catalytic reactor 36, that is the effluent fed through line 33 or line 45 for a bottom feed, to the shell side of the heat exchanger 14. As a result, the ethylene oxide-ammonia reaction mixture is heated by passage through the tube side of the heat exchanger 14 to a temperature which is considered desirable for effecting the adiabatic reaction of ethylene oxide with ammonia under supercritical fluid conditions. For example, the feed stream to the reactor is brought to a temperature of about 136° C. and 3,000 psia. It is then fed into tubular reactor 10 having, for example, a length to diameter ratio of 40:1 and which contains in the entry port thereof a swirling device as described in copending application Ser. No. 259,899, filed May 4, 1981. The continuous homogeneous fluid stream removed from reactor 10 is in the form of a supercritical fluid. The temperature and pressure of the fluid is sufficient to effect the supercritical state, such as a temperature of 170° C. and a pressure of 3,000 psia. The pressure in the stream is controlled by a pressure reducing valve, not shown, and is fed to interconnect with the fluid from line 19. The fluid from line 19 can contain the monoethanolamine recycle or a mixture of monoethanolamine recycle and ammonia which is also recycled or simply ammonia from recycled ammonia. In the preferred practice of the invention, the monoethanolamine recycle is mixed with some of the ammonia recycle and the combination is fed through line 19 to effect admixture with the effluent from reactor 10, that is the homogeneous fluid stream. The control of ammonia recycle to line 19 is effected by valve 13 located in line 21. The control for monoethanolamine addition to line 21 is effected by valve 23 located in line 20. If it is desired to introduce the monoethanolamine recycle at a later stage, then valve 23 can be closed thereby diverting flow of the monoethanolamine recycle through line 27. In such a case, valve 25 will be opened and allow the flow of the monoethanolamine recycle to a later stage in the process scheme. The admixture of the monoethanolamine recycle and the homogeneous fluid stream is achieved upon contact of line 19 with line 11 through which the homogeneous fluid stream is passed. The admixture is thereafter fed to heat exchanger 12 for the purpose of further reducing the temperature of the mix stream in line 11 to a desired temperature for the gas-liquid phase separation to be effected in the high pressure separator 30. The temperature reduction is effected by both the reduced temperature of the monoethanolamine recycle stream and any ammonia which is also recycled therewith into line 19 and thereafter into line 11. Further reduction in the temperature may be thereafter obtained by heat exchanger 12 to effect the desired temperature for effective gas-liquid separation under the conditions of high pressure which are existing in separator 30. The pressure in line 11 and separator 30 is controlled so as to effect, in coordination with the temperature therein, separation of the homogeneous fluid stream from reactor 10. The effluent vapor taken from the top of separator 30 is fed through line 34 to a heat exchanger (not shown) whereby to increase the temperature of the effluent stream which at this instance is characterized as the amination feed stream. By increasing the temperature, while maintaining a pressure of from about 1500 to about 2500 psi, and preferably about 2200 psia from the amination feed stream, the amination feed stream is converted into a supercritical fluid stream. This supercritical fluid stream is fed through line 34 into the top of amination reactor 36 which contains a fixed bed of rhenium-nickel catalyst containing boron supported upon a diatomaceous earth particulate support.

Alternatively, the amination feed stream may be advantageously fed through line 33 controlled by valve 55 into the bottom of amination reactor 36 so as to effect an upward flow of the amination feed stream through the catalyst bed contained therein during the amination reaction.

In order to provide the necessary hydrogen promoter to the reaction, hydrogen which is within the system is recycled through hydrogen compressor 24 into the upper portion of the high pressure separator 30 through line 22 and is thereafter carried with the amination feed stream through line 34, or alternatively line 33, into reactor 36.

The effluent from reactor 36 is passed into line 33, or alternatively line 45, and thereafter through the shell side of the heat exchanger used for preheating the ammonia-ethylene oxide reaction mixture as described previously, designated in the drawing as heat exchanger 31, for convenience sake. Heat exchanger 31 depicts the shell side of the same heat exchanger previously characterized as heat exchanger 14 which characterizes the tube side thereof. The reaction product effluent from reactor 36 is thereafter passed through line 35 into an ammonia flash tank 38 for the purpose of separating ammonia and hydrogen from the effluent liquid stream. The ammonia and hydrogen are taken off through line 28 and subsequently separated whereby the ammonia is fed through ammonia recycle compressor 26 and then into line 18 for subsequent recycle or it is passed to line 29 for eventual introduction into line 18, also for ammonia recycle, as described previously. The hydrogen is fed into a recycle compressor 24 so that the hydrogen can be recycled to separator 30 as described previously. The bottoms from flash tank 38 are fed through line 39 into which the bottoms from high pressure separator 30 are also fed by way of line 32 and the admixture is fed into a second flash separator, 37, for additional separation of ammonia to be recycled through line 18 by way of line 43 and ammonia recycle compressor 26. The bottoms from separator 37 is fed to an ammonia stripping still 40 through line 41 for final removal of ammonia from the amine reaction product mixture. The bottoms from the still 40 is passed through line 42 into distillation column 50 maintained at a temperature sufficient to remove the water contained in the reaction through line 49. The heavies from the reaction are recovered from distillation column 50 through line 44 and passed to still 52 for the recovery of ethylenediamine by way of line 51. The heavies from that distillation are removed through line 54 into piperazine still 56 from which piperazine is recovered through line 57. The bottoms from that separation are removed through line 53 and passed to still 58 for the recovery of monoethanolamine which is recycled by way of line 20 for eventual addition to the homogeneous fluid stream either prior to or after the high pressure separator 30. The bottoms of that separation are passed from line 59 into a series of refining columns for recovering each of the various components of the stream.

DETAILED DESCRIPTION

EXAMPLE 1

The reaction system and apparatus shown in the drawing and discussed above, comprising an adiabatic, tubular ethylene oxide/ammonia reactor, an amination catalytic reactor, and associated equipment, is used in this run. In this run, a liquid ethylene oxide feed of 220 moles per hour is mixed with a liquid ammonia-water mixture (98 percent $NH_3$, 2 percent water) to give an ammonia to ethylene oxide mole ratio of 30:1. The mixed ammonia/ethylene oxide feed is pumped into the first reactor stage of reactor 10, which is a four stage adiabatic, tubular reactor having a 40:1 length to diameter ratio, after preheating to a temperature of about 135° C. The pressures in the reactor stages are controlled to maintain the flowing stream in a single, swirling, supercritical fluid phase having an average reaction mixture density of 21.5 lbs/ft$^3$. The pressure at the outlet of the final reactor stage of reactor 10 is 3000 psig (204 atm.) and the temperature of the product mixture is 170° C. after a residence time within the reactor of about 20 minutes.

The homogeneous product mixture stream from the ethylene oxide/ammonia reactor 10 contains about 95 mole percent ammonia, 1.9 mole percent water, 2.4 mole percent monoethanolamine, 0.4 mole percent diethanolamine and less than 0.1 mole percent triethanolamine. The homogeneous fluid stream in line 11 is depressurized to 2200 psig (150 atm.) and is mixed with a monoethanolamine recycle stream carried in line 19 from line 20 containing 99 mole percent monoethanolamine and an ammonia recycle stream containing about 98 mole percent ammonia and 2 mole percent water carried in line 19 from lines 18 and 21, and then preheated to a temperature of 155° C. before being fed to a 3½ foot diameter high pressure separator, 30, which is maintained at a pressure of 2200 psig (150 atm.). A recycle stream containing about 80 mole percent hydrogen and 20 mole percent ammonia is also fed to the product mixture in high pressure separator 30 through line 22.

The overhead stream from the high pressure separator is heated to 170° C. to form a homogeneous single phase before being fed to the catalytic amination reactor 36. The overhead stream from the separator 30, contains about 7.2 mole percent hydrogen, 87.0 mole percent ammonia, 1.4 mole percent water, 4.3 mole percent monoethanolamine, 0.1 mole percent diethanolamine and less than 0.01 mole percent triethanolamine.

Amination reactor 36 is a 7 foot diameter vertical reactor containing an 1100 ft.$^3$ bed of solid catalyst comprising 7.0% nickel; 1.86% rhenium; 1.44% boron on a silica-alumina support. The feed stream enters the bottom thereof through line 33 and valve 55 and flows upward through the catalyst bed while being maintained in a single supercritical fluid phase at a temperature of 170° C. and a pressure of 2200 psi (150 atm.).

The effluent taken from the top of the amination reactor 36 through line 45 comprises a single phase fluid stream containing about 7.2 mole percent hydrogen, 85 mole percent ammonia, 3.1 mole percent water, 1.3 mole percent ethylenediamine, 0.1 mole percent diethylenediamine (piperazine), 0.1 mole percent diethylenetriamine, 2.6 mole percent monoethanolamine, 0.1 mole percent diethanolamine and less than 0.01 mole percent each of aminoethylpiperazine, aminoethylethanolamine, and triethanolamine. This stream is cooled to 150° C. and depressurized to 400 psia (27.2atm.) before being fed through a 6 foot diameter flash separator 38 where unreacted ammonia is recovered for recycling back to the ethylene oxide-ammonia reactor 10 and recovered hydrogen is recycled back to the high pressure separator 30, respectively. The liquid bottoms from the flash separator 38 contains about 70 mole percent ammonia, 12 mole percent water, 5.3 mole percent ethylenediamine, 0.4 mole percent piperazine, 10.5 mole percent monoethanolamine, 0.3 mole percent diethylenetriamine, 0.04 mole percent aminoethylpiperazine, 0.3 mole percent aminoethylethanolamine, 0.36 mole percent diethanolamine and less than 0.05 mole percent of other amine products. This stream is combined in line 39 with the liquid bottoms product from the high pressure separator, 30, containing about 61 mole percent ammonia, 4.3 mole percent water, 24.7 mole percent monoethanolamine, 4.1 mole percent diethanolamine and 0.6 mole percent triethanolamine, depressurized to 225 psia (15.3 atm.) and heated to 80° C. in a flash separator, 37, where about 80 percent of the remaining unreacted ammonia is removed and recycled to the ethylene oxide/ammonia reactor 10, through line 18.

The liquid bottoms from the flash separator 37 is fed to ammonia stripping still 40, a standard distillation column operating with a pressure of 50 psia to remove the remaining unreacted ammonia and about 40 percent of the water for recycle.

The bottom stream from the distillation column 40, comprising the mixed products contains about 24 mole percent water and 18 mole percent ethylenediamine, 1.3 mole percent piperazine, 1.2 mole percent diethylenetriamine, 0.1 mole percent aminoethylpiperazine, 0.1 mole percent hydroxyethylpiperazine in addition to 50 mole percent monoethanolamine, 1.0 mole percent of aminoethylethanolamine, 3.5 mole percent of diethanolamine and less than 0.5 mole percent of triethanolamine. This stream is then separated by standard distillation techniques into component alkanolamines and alkylemamines for recovery or recycle. Monoethanolamine is recycled through line 20 to and mixed with the homogeneous fluid product mixture in line 11. The run produces about 115 moles per hour of ethylenediamine, about 8 moles per hour of piperazine, about 7.6 moles per hour of diethylenetriamine and about 7.0 moles per hour of aminoethylethanolamine. About 23 moles per hour of diethanolamine is also recovered.

We claim:

1. A continuous process for the manufacture of ethylenediamine which comprises:
   (A) providing (1) a continuous homogeneous fluid stream under pressure, which stream comprises ammonia, monoethanolamine, diethanolamine and triethanolamine as produced by the direct reaction of ethylene oxide and ammonia in which the number of moles of ammonia substantially exceeds the molar concentration of alcoholic hydroxyl groups present in such steams; (2) a continuous recycle stream consisting essentially of monoethanolamine; (3) an amination zone comprising a solid amination catalyst; and (4) a separation zone for separating monoethanolamine from the amination product stream removed from the amination zone which monoethanolamine forms said recycle stream;
   (B) feeding said recycle stream under pressure to said fluid stream to form a continuous amination feed stream under pressure;
   (C) feeding the amination feed stream to the amination zone under sufficient pressure to assure flow through the amination zone but at lower pressure than said homogeneous fluid stream and to form an amination product stream containing ethylenediamine therein;
   (D) separating monoethanolamine from the amination product stream to form said recycle stream; and
   (E) continuously recovering ethylenediamine from said amination product stream; wherein said amination feed stream contains at least 70 weight percent monoethanolamine, based on the weight of the ethanolamines therein; the moles of ammonia in the amination feed stream exceeds the molar concentration of alcoholic hydroxyl groups in said amination feed stream; and the amination feed stream contains at least a 5% increase in the concentration of monoethanolamine over that contained in said fluid stream.

2. The process of claim 1 wherein said ethylene oxide-ammonia product mixture stream is in a single, supercritical fluid phase.

3. The process of claim 1 wherein the amination feed stream in the amination zone is a homogeneous fluid.

4. The process of claim 1 wherein the amination feed stream in the amination zone is in a single, supercritical fluid phase.

5. The process of claim 1 wherein the solid amination catalyst in the amination zone comprises nickel.

6. The process of claim 1 wherein the solid amination catalyst in the amination zone comprises nickel-rhenium on a support medium.

7. The process of claim 1 wherein said continuous amination feed stream contains hydrogen.

8. The process of claim 6 wherein the amination feed stream contains hydrogen.

* * * * *